(12) United States Patent
Wang et al.

(10) Patent No.: US 10,085,988 B1
(45) Date of Patent: Oct. 2, 2018

(54) AGLAROXIN C AND DERIVATIVES AS HCV ENTRY INHIBITORS

(71) Applicants: SRI International, Menlo Park, CA (US); Trustees of Boston University, Boston, MA (US)

(72) Inventors: Tony Tianyi Wang, Harrisonburg, VA (US); Shufeng Liu, Harrisonburg, VA (US); Wenyu Wang, Boston, MA (US); Neil Lajkiewicz, Garnet Valley, PA (US); John A. Porco, Jr., Brookline, MA (US)

(73) Assignees: SRI International, Menlo Park, CA (US); Trustees of Boston University, Boston, MA (US)

( * ) Notice: Subject to any disclaimer, the term of this patent is extended or adjusted under 35 U.S.C. 154(b) by 0 days.

(21) Appl. No.: 15/269,886

(22) Filed: Sep. 19, 2016

Related U.S. Application Data

(60) Provisional application No. 62/220,710, filed on Sep. 18, 2015.

(51) Int. Cl.
| | | |
|---|---|---|
| *A61K 31/519* | (2006.01) | |
| *A61K 31/343* | (2006.01) | |
| *A61K 31/36* | (2006.01) | |
| *C07D 491/048* | (2006.01) | |
| *A61K 39/395* | (2006.01) | |

(52) U.S. Cl.
CPC .......... *A61K 31/519* (2013.01); *A61K 31/343* (2013.01); *A61K 39/395* (2013.01); *C07D 491/048* (2013.01)

(58) Field of Classification Search
CPC ............... A61K 31/519; A61K 31/343; A61K 2300/00; A61K 39/395; A61K 2039/505; A61K 38/1774; A61K 38/191; A61K 39/3955; A61K 45/06; C07D 491/048
See application file for complete search history.

(56) References Cited

PUBLICATIONS

Liu et al. (EBioMedicine 2 (2015) 1600-1606, available online on Sep. 14, 2015).*
Polier et al. (Chemistry and Biology 19, 2012, 1093-1104).*
Dang et al. (Virology Journal, 2011, 8: pp. 1-6).*
Dubuisson J, Rice CM. Hepatitis C Virus Glycoprotein Folding: Disulfide Bond Formation and Association with Calnexin. J Virol. 1996;70(2):778-786. Epub Feb. 1, 1996 PubMed PMID: 8551615.
Falkowska E, Kajumo F, Garcia E, Reinus J, Dragic T. Hepatitis C Virus Envelope Glycoprotein E2 Glycans Modulate Entry, CD81 binding, and neutralization. J Virol. 2007;81(15):8072-8079. Epub May 18, 2007 doi: JVI.00459-07.
Flint M, Maidens C, Loomis-Price LD, Shotton C, Dubuisson J, Monk P, et al. Characterization of Hepatitis C Virus E2 Glycoprotein Interaction with a Putative Cellular Receptor, CD81. J Virol. 1999;73(8):6235-6244. PubMed PMID: 10400713.
Helle F, Goffard A, Morel V, Duverlie G, McKeating J, Keck ZY, et al. The Neutralizing Activity of Anti-Hepatitis C Virus Antibodies is Modulated by Specific Glycans on the E2 Envelope Protein. J Virol. 2007;81(15):8101-8111. Epub May 25, 2007.

(Continued)

*Primary Examiner* — Savitha M Rao

(57) ABSTRACT

A rocaglamide or a rocaglate derivative, particularly aglaroxin C, blocks hepatitis C virus (HCV) entry with improved potency and therapeutic index.

13 Claims, 10 Drawing Sheets

(56) References Cited

PUBLICATIONS

Helle F, Vieyres G, Elkrief L, Popescu CI, Wychowski C, Descamps V, et al. Role of N-linked Glycans in the Functions of HCV Envelope Proteins Incorporated into Infectious Virions. J Virol. 2010; pp. 11905-11915; pub Sep. 17, 2010. doi: JVI.01548-10 [pii]10.1128/JVI.01548-10. PubMed PMID: 20844034.

Lajkiewicz NJ, Cognetta AB, 3rd, Niphakis MJ, Cravatt BF, Porco JA, Jr. Remodeling Natural Products: Chemistry and Serine Hydrolase Activity of a Rocaglate-Derived Beta-Lactone. J Am Chem Soc. 2014;136(6):2659-64. Epub Jan. 23, 2014. doi: 10.1021/ja412431g. PubMed PMID: 24447064; PubMed Central PMCID: PMC3978386.

Lee SK, Cui B, Mehta RR, Kinghorn AD, Pezzuto JM. Cytostatic Mechanism and Antitumor Potential of Novel 1H-cyclopenta[b-]benzofuran Lignans Isolated from Aglaia elliptica. Chemico-biological interactions. 1998;115(3):215-228. Epub Dec. 16, 1998. PubMed PMID: 9851291.

Ohse T, Ohba S, Yamamoto T, Koyano T, Umezawa K. Cyclopentabenzofuran Lignan Protein Synthesis Inhibitors from Aglaia odorata. Journal of natural products. 1996;59(7):650-2. Epub Jul. 1, 1996. doi: 10.1021/np960346g. PubMed PMID: 8759160.

Parodi AJ. Protein Glucosylation and its Role in Protein Fplding. Annual Review of Biochemistry. 2000;69:69-93. Epub Aug. 31, 2000. doi: 10.1146/annurev.biochem.69.1.69. PubMed PMID: 10966453.

Patman G. Rectal cancer: What surgery is best? Nat Rev Gastroenterol Hepatol. 2015;12(5):252. Epub Apr. 22, 2015. id: 10.1038/nrgastro.2015.66. PubMed PMID: 25895826.

Patman G. Microbiota: Sewage Comes up Smelling like Roses for Microbiota Research. Nat Rev Gastroenterol Hepatol. 2015;12(5):252. Epub Mar. 18, 2015. doi: 10.1038/nrgastro.2015.48. PubMed PMID: 25782094.

Tsukuma H, Hiyama T, Tanaka S, Nakao M, Yabuuchi T, Kitamura T, et al. Risk Factors for Hepatocellular Carcinoma Among Patients with Chronic Liver Disease. The New England journal of medicine. 1993;328(25):1797-801. Epub Jun. 24, 1993. doi: 10.1056/NEJM199306243282501. PubMed PMID: 7684822.

Kontorinis N, Agarwal K, & Dieterich DT (2004) Current status of the use of growth factors and other adjuvant medications in patients receiving peginterferon and ribavirin. Rev Gastroenterol Disord 4 Suppl 1:S39-47.

Ray K (2015) Therapy: Retreatment of HCV infection in DAA nonresponders. Nat Rev Gastroenterol Hepatol 12 (5):252.

Pawlotsky JM, Feld JJ, Zeuzem S, & Hoofnagle JH (2015) From non-A, non-B hepatitis to hepatitis C virus cure. J Hepatol 62(15):587-599.

Lindenbach BD, et al. (2005) Complete replication of hepatitis C virus in cell culture. Science 309(5734):623-626.

Kato T, et al. (2005) Nonhepatic cell lines HeLa and 293 support efficient replication of the hepatitis C virus genotype 2a subgenomic replicon. J Virol 79(1):592-596.

Zhang J, et al. (2004) CD81 is required for hepatitis C virus glycoprotein-mediated viral infection. J Virol 78(3): 1448-1455.

Cormier EG, et al. (2004) CD81 is an entry coreceptor for hepatitis C virus. Proceedings of the National Academy of Sciences of the United States of America 101(19):7270-7274.

Bartosch B, Dubuisson J, & Cosset FL (2003) Infectious hepatitis C virus pseudo-particles containing functional El-E2 envelope protein complexes. J Exp Med 197(5):633-642.

Petracca R, et al. (2000) Structure-function analysis of hepatitis C virus envelope-CD81 binding, J Virol 74 (10):4824-4830.

Meertens L, Bertaux C, & Dragic T (2006) Hepatitis C virus entry requires a critical postinternalization step and delivery to early endosomes via clathrin-coated vesicles. J Virol 80(23):11571-11578.

Hsu M,et al. (2003) Hepatitis C virus glycoproteins mediate pH-dependent cell entry of pseudotyped retroviral particles. Proceedings of the National Academy of Sciences of the United States of America 100(12):7271-7276.

Selby MJ, Glazer E, Masiarz F, & Houghton M (1994) Complex processing and protein:protein interactions in the E2: NS2 region of HCV. Virology 204(1):114-122.

Pileri P, et al. (1998) Binding of hepatitis C virus to CD81. Science 282(5390):938-941.

Scarselli E, et al. (2002) The human scavenger receptor class B type I is a novel candidate receptor for the hepatitis C virus. The EM BO journal 21(19):5017-5025.

Evans MJ, et al. (2007) Claudin-1 is a hepatitis C virus co-receptor required for a late step in entry. Nature 446 (7137):801-805.

Liu S, et al. (2009) Tight Junction Proteins Claudin-1 and Occludin Control Hepatitis C Virus Entry and are Downregulated during Infection to Prevent Superinfection. J Virol 83(4):2011-2014.

Ploss A, et al. (2009) Human occludin is a hepatitis C virus entry factor required for infection of mouse cells. Nature 457(7231):882-886.

Lupberger J, et al. (2011) EGFR and EphA2 are host factors for hepatitis C virus entry and possible targets for antiviral therapy. Nature medicine 17(5):589-595.

Sainz B, Jr., et al. (2012) Identification of the Niemann-Pick Cl-like 1cholesterol absorption receptor as a new hepatitis 2, virus entry factor Nature medicine 18(2):281-285.

Zona L, et al. (2013) HRas signal transduction promotes hepatitis C virus cell entry by triggering assembly of the host tetraspanin receptor complex. Cell host & microbe 13(3):302-313.

McClung JK, et al. (1989) Isolation of a cDNA that hybrid selects antiproliferative mRNA from rat liver. Biochemical and biophysical research communications 164(3): 1316-1322.

Montano MM, et al. (1999) An estrogen receptor-selective coregulator that potentiates the effectiveness of antiestrogens and represses the activity of estrogens. Proceedings of the National Academy of Sciences of the United States of America 96(12):6947-6952.

Lan JF, et al. (2013) Prohibitin Interacts with envelope proteins of white spot syndrome virus and prevents infection in the red swamp crayfish, *Procambarus clarkii*. J Virol 87(23):12756-12765.

Wintachai P, et al. (2012) Identification of prohibitin as a Chikungunya virus receptor protein. Journal of medical virology 84(11):1757-1770.

Kuadkitkan A, Wikan N, Fongsaran C, & Smith DR (2010) Identification and characterization of prohibitin as a receptor protein mediating DENV-2 entry into insect cells. Virology 406(1):149-161.

Emerson V, et al. (2010) Identification of the cellular prohibitin 1/prohibitin 2 heterodimer as an interaction partner of the C-terminal cytoplasmic domain of the HIV-1 glycoprotein. J Virol 84(3):1355-1365.

Back JW, et al. (2002) A structure for the yeast prohibitin complex: Structure prediction and evidence from chemical crosslinking and mass spectrometry. Protein science: a publication of the Protein Society 11(10):2471-2478.

Mishra S, Murphy LC, Nyomba BL & Murphy LJ (2005) Prohibitin: a potential target for new therapeutics. Trends in molecular medicine 11(4):192-197.

Theiss AL & Sitaraman SV (2011) the role and therapeutic potential of prohibitin in disease. Biochimica et biophysica acta 1813(6)1137-1143.

Kim do K, et al. (2013) The scaffold protein prohibitin is required for antigen-stimulated signaling in mast cells. Science signaling 6(292):ra80.

Kolonin MG, Saha PK, Chan L, Pasqualini R, & Arap W (2004) Reversal of obesity by targeted ablation of adipose tissue. Nature medicine 10(6):625-632.

Diao J, et al. (2012) Hepatitis C virus induces epidermal growth factor receptor activation via CD81 binding for viral internalization and entry. Journal of virology 86(20):10935-10949.

Polier G, et al. (2012) The natural anticancer compounds rocaglamides inhibit the Raf-MEK-ERK pathway by targeting prohibitin 1and 2. Chem Biol 19(9):1093-1104.

Udom Kokpol BV, Jim Simpson and Rex T. Weavers (1994) Isolation and X-ray structure determination of a novel pyrimidinone from Aglaia odorata. J. Chem. Soc., Chem. Commun. (6):773-774.

Rajalingam K & Rudel T (2005) Ras-Raf signaling needs prohibitin. Cell Cycle 4(11):1503-1505.

(56) References Cited

OTHER PUBLICATIONS

Yang W, et al. (2008) Correlation of the tight junction-like distribution of claudin-1 to the cellular tropism of HCV. The Journal of biological chemistry 283(13)(13): 8643-8653.

Chiu CF, et al. (2013) Raf activation by Ras and promotion of cellular metastasis require phosphorylation of prohibitin in the raft domain of the plasma membrane. Oncogene 32(6):777-787.

Kim S, Salim AA, Swanson SM, & Kinghorn AD (2006) Potential of cyclopenta(b)benzofurans from *Aglaia* species in cancer chemotherapy. Anti-cancer agents in medicinal chemistry 6(4):319-345.

Ebada SS, Lajkiewicz N, Porco JA, Jr., Li-Weber M, & Proksch P (2011) Chemistry and biology of rocaglamides (= flavaglines) and related derivatives from *Aglaia* species (meliaceae). Progress in the chemistry of organic natural products 94:1-58.

Roche SPC, R.; Pelletier, J.; Porco, J.A., Jr. (2010) Biomimetic Photocycloaddition of 3-Hydroxyflavones: Synthesis and Evaluation of Rocaglate Derivatives as Inhibitors of Eukaryotic Translation. Angew. Chem. Int. Ed 49:6533-6538.

Rodrigo CM, Cencic R, Roche SP, Pelletier J, & Porco JA (2012) Synthesis of rocaglamide hydroxamates and related compounds as eukaryotic translation inhibitors: synthetic and biological studies. J Med Chem 55(1):558-562.

Si Y, et al. (2012) A human claudin-1-derived peptide inhibits hepatitis C virus entry. Hepatology 56(2):507-515.

Gerard B, Sangji S, O'Leary DJ, & Porco JA, Jr. (2006) Enantioselective photocycloaddition mediated by chiral Bronsted acids: asymmetric synthesis of the rocaglamides. J Am Chem Soc 128(24):7754-7755.

Santagata S, et al. (2013) Tight coordination of protein translation and HSF1 activation supports the anabolic malignant state. Science 341(6143):1238303.

Stone S.; Lajkiewicz NW, L.; Hilmy, A.;Porco, J.A., Jr. (2015) Biomimetic Kinetic Resolution: Highly Enantio- and Diastereoselective Transfer Hydrogenation of Aglain Ketones to Access Flavagline Natural Products. J. Am. Chem. Soc 137:525-530.

Baumann B, Bohnenstengel F, Siegmund D, Wajant H, Weber C, Herr I, et al., Rocaglamide Derivatives are Potent Inhibitors of NF-kappa B Activation in T-cells. The Journal of biological chemistry. 2002;277(47):44791-44800. Epub Sep. 19, 2002.

Choukhi A, Ung S, Wychowski C, Dubuisson J., Involvement of Endoplasmic Reticulum Chaperones in the Folding of Hepatitis C Virus Glycoproteins. J Virol. 1998;72(5):3851-3858. Epub Apr. 29, 1998 PubMed PMID: 9557669.

Cencic R, et al. (2010) Synergistic effect of inhibiting translation initiation in combination with cytotoxic agents in acute myelogenous leukemia cells. Leuk Res 34(4):535-541.

Rozelle DK, Filone CM, Kedersha N, & Connor JH (2014) Activation of stress response pathways promotes formation of antiviral granules and restricts virus replication. Mol Cell Biol 34(11):2003-2016.

Wintachai P, et al. (2015) Assessment of flavaglines as potential chikungunya virus entry inhibitors. Microbial Immunol 59(3):129-141.

* cited by examiner

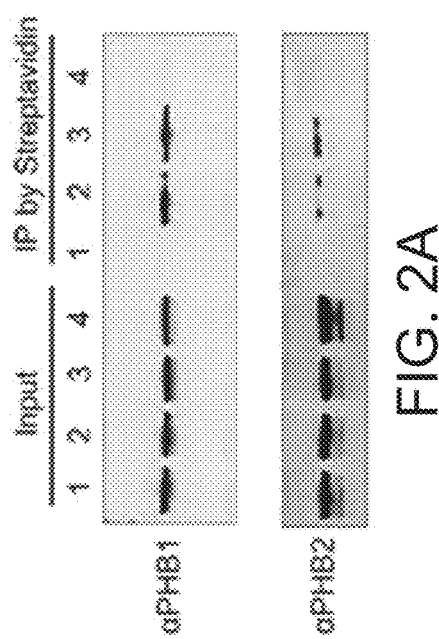
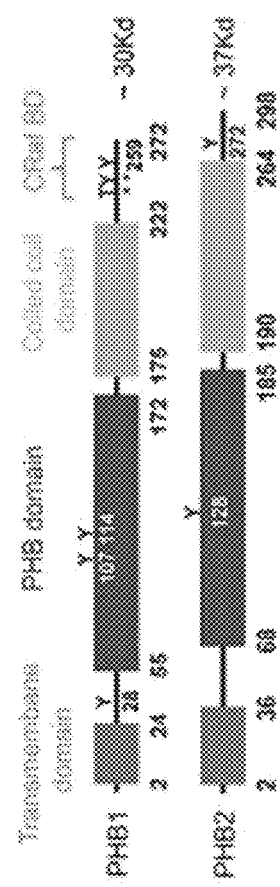
FIG. 2A
FIG. 2B
FIG. 2C

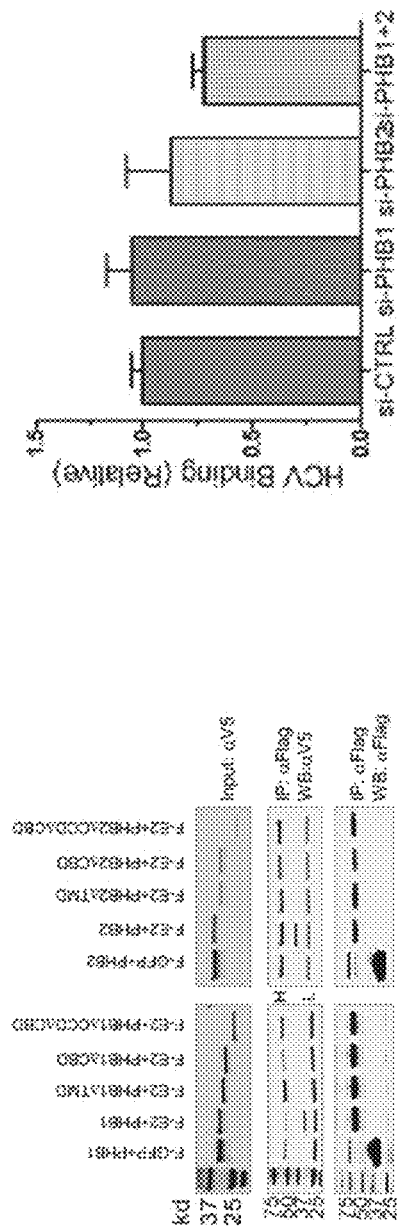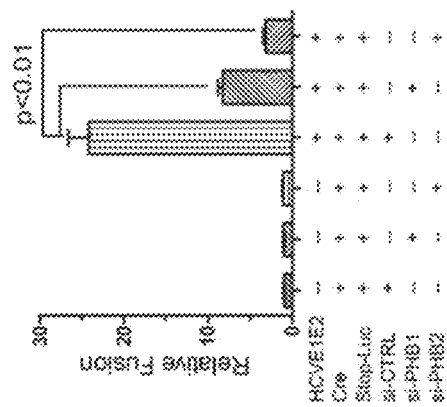
FIG. 2E
FIG. 2F
FIG. 2G

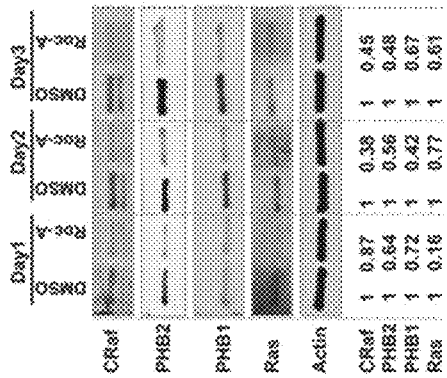
FIG. 3A
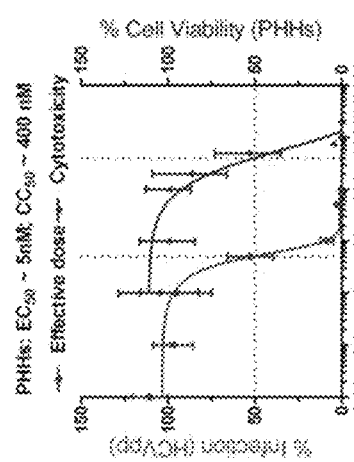
FIG. 3C
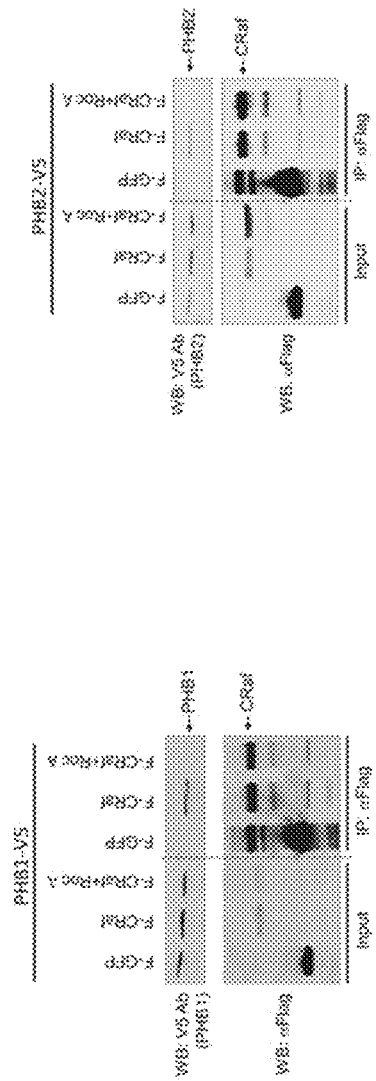
FIG. 3B
FIG. 3D

AGLAROXIN C AND DERIVATIVES AS HCV ENTRY INHIBITORS

CROSS-REFERENCE TO RELATED APPLICATIONS

This application claims the benefit of, and incorporates herein in its entirety, U.S. Provisional Patent Application Ser. No. 62/220,710 filed on Sep. 18, 2015 and entitled "AGLAROXIN C AND DERIVATIVES AS HCV ENTRY INHIBITORS."

STATEMENT REGARDING FEDERALLY SPONSORED RESEARCH

This invention was made with government support under award number RO1DK088787 awarded by the National Institute of Diabetes and Kidney Diseases of the National Institutes of Health and support under award number GM 073855 awarded by the National Institute of General Medical Sciences of the National Institutes of Health. The government has certain rights in the invention

BACKGROUND OF THE INVENTION

The field of the invention relates to a class of small molecule compounds that inhibit virus infection. Hepatitis C virus (HCV) is a human pathogen that primarily infects human hepatocytes and causes chronic liver diseases. It remains unclear whether direct-acting antiviral (DAA)-containing regimens fully prevent pathology or restore normal immunity. Moreover, with continuous and expanded usage of DAAs, HCV is expected to become progressively more drug resistant, thereby eroding the efficacy of DAAs. Lastly, most DAAs are hardly affordable to patients in resource-limited countries. For these reasons, druggable host targets and new lead compounds are highly desirable.

HCV entry is a multifaceted target for intervention. HCV encodes ten viral proteins to complete its life cycle. Viral glycoproteins E1 and E2 together form spikes on the viral envelope, which then engage with cell surface molecules and trigger the endocytosis of the viral particle. In addition, E2 interacts with HCV nonstructural protein 2 (NS2) and plays an important role in virus morphogenesis. Recent advances have suggested that HCV enters hepatocytes in a step-wise fashion by utilizing multiple cellular membrane proteins, including CD81, scavenger receptor BI (SRBI), claudin-1 (CLDN1), occludin (OCLN), epidermal growth factor receptor (EGFR), and cholesterol-uptake receptor Niemann-Pick C1-like 1 (NPC1L1). Further, the GTPase HRas acts as a signal transducer for EGFR-mediated HCV entry by regulating lateral membrane diffusion of CD81 which then enables tetraspanin receptor complex assembly.

SUMMARY OF THE INVENTION

Applicants' disclosure describe a class of therapeutic agents that inhibits HCV, dengue virus (DENV), and chikungunya virus (CHIKV) entries by targeting the prohibitin-CRaf pathway. Prohibitin 1 (PHB1) is a ubiquitously expressed protein displaying antiproliferative activity. Prohibitin 2 (PHB2), also named repressor of estrogen receptor activity (REA), suppresses estrogen receptor (ER)-dependent gene activation. Interestingly, PHB has been implicated in the entry process of dengue and chikungunya virus (CHIKV) and also binds to HIV-1 glycoprotein and envelope proteins of the white spot syndrome virus.

Embodiments of Applicants' disclosure describe rocaglamide A and aglaroxin C and their derivatives in inhibiting HCV, DENV, and CHIKV entries. Further, embodiments of Applicants' disclosure describe effectiveness of chirality of certain compounds.

BRIEF DESCRIPTION OF THE DRAWINGS

FIGS. 2A-2G illustrate that PHB1 and 2 mediate HCV entry via a novel mechanism. (A) Huh7.5.1 cells were surface biotinylated as described in the Materials and Methods section. IP was done using streptavidin agarose beads. The presence of PHB1 and PHB2 was detected by Western blotting. Lane 1, no biotin labeling; lane 2, biotin labeled; lane 3, HCVcc infected cells labeled with biotin; lane 4, RocA (20 nM) treated cells labeled with biotin. Of note, because Roc-A treatment decreased the total cellular PHB1 and 2 (Shown in FIG. 3B), we intentionally used twice as many cells as starting materials for the Roc-A treated group (Lane 4) in order to achieve similar amount of prohibitins in the input in comparison to the levels in other lanes. (B) Domain organization of PHBs. (C) Surface biotinylation assay on individual PHB deletion mutants. (D) Confocal images of PHB deletion mutants. Green, PHB mutants; Red, mitotracker. (E), co-IP studies of Flag-E2 (F-E2) and VS-tagged PHB deletion mutants. (F) Real-time quantification of HCV RNA bound to cells in which PHB1 or PHB2were knocked down. Results were calculated as relative RNA copies with numbers obtained from si-CTRL transfected cells set to 1 (mean±SD, $* p<0.05$). (G) 293 T-CLDN1 cells expressing HCV E1E2 and Cre were fused to Huh7.5.1 cells that were transfected with siRNA and Stop-Luc expressing plasmid. Luciferase activity was determined 24 h after mixing (mean±SD, $*p<0.05$).

FIGS. 3A-3G show that rocaglamide A (Roc-A) potently inhibits HCV infection. (A) PHHs seeded in a 48-well plate were treated with Roc-A or DMSO and then infected by HCVpp. EC50and CC50 (50% cytotoxicity dose) were calculated based on the fitted Sigmoid curves. (B) Huh7.5.1 cells were treated with Roc-A (20 nM) or DMSO for 1, 2, and 3 days. Cellular PHB1, PHB2, CRaf, and Ras were detected by Western blotting. Numbers shown below Western blot gel images indicate the relative protein levels quantified by Odyssey imaging system (LI-COR Biosciences). (C-D) Flag-CRaf (F-CRaf) and V5-tagged PHB1 & 2 were co-transfected into 293T cells and then left untreated or treated with Roc-A (20 nM) before immunoprecipitation with anti-Flag antibody. The pulled-down PHB1 & 2 as well as CRaf were detected by immunoblotting. (E) Different inhibitory profiles of the (+)- and(−)-Roc-A enantiomers on HCVcc infection. (F) A CMV-luciferase reporter construct was transfected into Huh7.5.1 cells. 24 h post-transfection each compound was added to the cells for 3 h at 2 µM. After removal of the compound, the cells were further incubated for 24 h followed by luciferase assay. (G) C10 (racemic aglaroxin C) inhibited HCV infection when added together with the virus. HCVcc-Luc was added to Huh7.5.1 cells at 37° C. and incubated for 3 h. At the indicated time points, 2µM of each compound or DMSO was added into the media and incubated for 3 h prior to removal. Infected cells were incubated at 37° C. for an additional 48 h prior to luciferase assay (mean of n=3; error bars, s.d.). Compound E2 (−)-NH hydroxamate, is a potent translation inhibitor (Rodrigo et al., 2012) and hence appeared to inhibit HCV no matter when added; compound C4 (±)-β-lactone (Lajkiewicz et al., 2014), was added as a negative control as it exerted negligible effect.

Figures 4A, 4B:
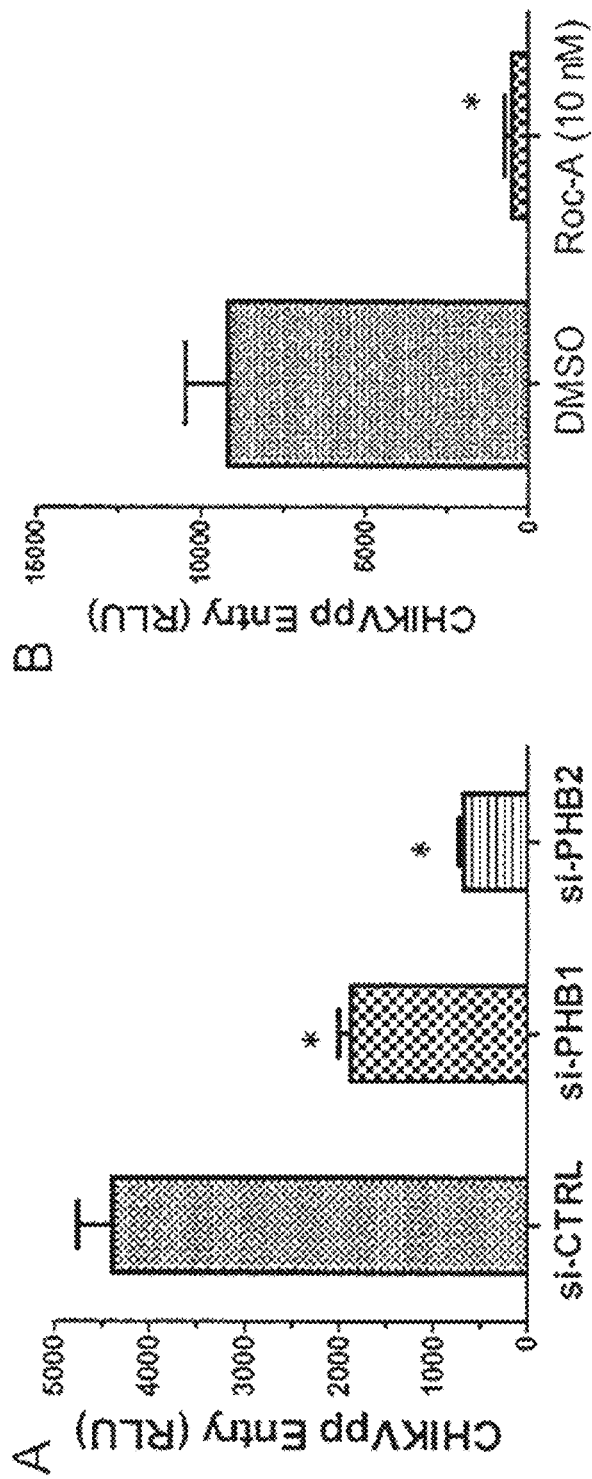

FIGS. 4A and 4B illustrate that PHBs are required for CHIKVpp entry. (A) Huh7.5.1 were transfected with indicated siRNA, followed by infection of CHIKVpp (mean±SD, *p<0.05). (B) Huh 7.5.1 cells were treated with DMSO or Roc-A (10 nM) and then infected by CHIKVpp for luciferase assay (mean±SD, *p<0.05).

Figure 5:
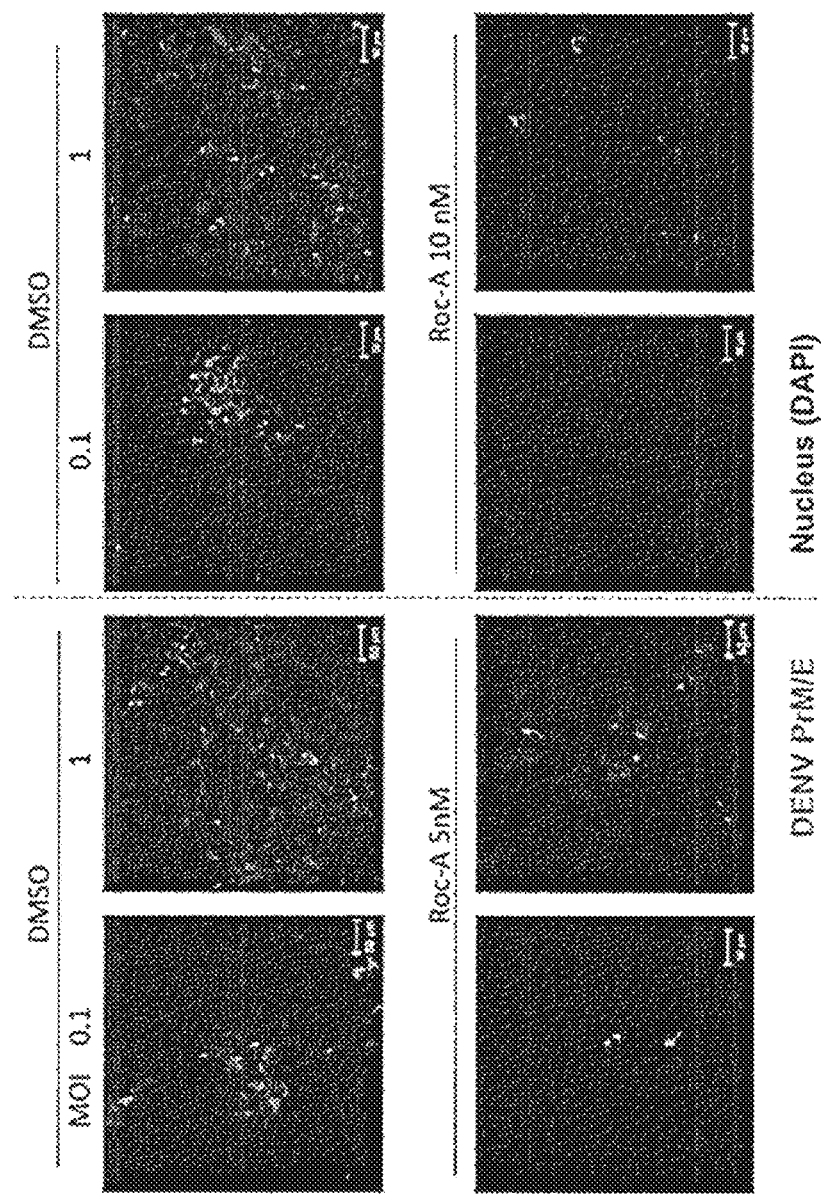

FIG. 5 shows that Roc-A treatment reduced DENV2 infection. Huh7.5.1 cells were treated by DMSO, Roc-A (5nM) or Roc-A (10nM) for 10 hours prior to infection by DENV2 (MOI 0.1 and 1). 36 hours post-infection, cells were fixed in methanol and immunostained for DENV prM/E (red). Notably in the Roc-A treated groups, not only did the number of infected cells decrease, but the size of the foci also significantly decreased in comparison to the DMSO-treated cells.

The foregoing and other aspects and advantages of the invention will appear from the following description. In the description, reference is made to the accompanying drawings that form a part hereof, and in which there is shown by way of illustration preferred embodiments of the invention. Such embodiments do not necessarily represent the full scope of the invention, however, and reference is made therefore to the claims and herein for interpreting the scope of the invention.

DETAILED DESCRIPTION OF THE PREFERRED EMBODIMENTS

Embodiments of the disclosure solve the issue of blocking HCV entry with improved potency and therapeutic index.

This invention is described with examples referring to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

For the terms "for example" and "such as," and grammatical equivalents thereof, the phrase "and without limitation" is understood to follow unless explicitly stated otherwise. As used herein, the term "about" is meant to account for variations due to experimental error. Numerical result of any measurement disclosed below is understood to be modified by the term "about," whether or not the term is explicitly used and unless explicitly stated otherwise.

The term "salt" refers to any ionic form of a compound and one or more counter-ionic species (cations and/or anions). The term "salt" additionally includes zwitterionic compounds (i.e., a molecule containing one more cationic and anionic species, e.g., zwitterionic amino acids). Counter ions present in a salt can include any cationic, anionic, or zwitterionic species. Examples of anions include, but are not limited to: chloride, bromide, iodide, nitrate, sulfate, bisulfate, sulfite, bisulfate, phosphate, acid phosphate, perchlorate, chlorate, chlorite, hypochlorite, periodate, iodate, iodite, hypoiodite, carbonate, bicarbonate, isonicotinate, acetate, trichloroacetate, trifluoroacetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, trifluormethansulfonate, ethanesulfonate, benzensulfonate, p-toluenesulfonate, p-trifluoromethylbenzenesulfonate, hydroxide, aluminates and borates. Examples of cations include, but are not limited to: monovalent alkali, metal cations, such as lithium, sodium, potassium, and cesium, and divalent alkaline earth metals, such as beryllium, magnesium, calcium, strontium, and barium. Also covered by this term are transition metal cations, such as gold, silver, copper and zinc, as well as non-metal cations, such as ammonium salts.

Polar surface area (PSA) of a molecule is defined herein as a surface sum over all polar atoms, primarily over oxygen and nitrogen with their attached hydrogens. PSA is used to measure a compound's ability to permeate cells in the art of medicinal chemistry.

The logP value of a compound, which is the logarithm of its partition coefficient between n-octanol and water log (coctanol/cwater), is a well-established measure of the compound's hydrophilicity. Low hydrophilicities and therefore high logP values cause poor absorption or permeation.

The term "pharmaceutically acceptable" is used to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "therapeutically effective dosage" of the compound is the amount that is required to inhibit HCV entry into cells in order to reduce the HCV infection rate to ≤about 10%. In other words, a "therapeutically effective dosage" of the compound is the amount needed to cause an effect in vivo that ≥about 90% of infection will be reduced. It is known in the art that the therapeutically effective dosage of a drug depends on the route of administration.

The scope of the present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety. Conventional methods for preparing salt forms are described, for example, in *Handbook of Pharmaceutical Salts: Properties, Selection, and Use*, Wiley-VCH, 2002

The compounds described below, including salts of such compounds, can be prepared using known organic synthesis techniques and can be synthesized according to any of numerous possible synthetic routes.

FIGS. 1A-1F indicate that PHB1 and 2 are pan-genomic HCV entry factors. PHB1 and 2 are found to be the most abundant proteins interacting with HCV E2 complex as detected by mass spectrometry during a comparative proteomics analysis of the HCV-infected human hepatoma cell line Huh7.5.1. To validate the results, immunoprecipitation using lysates from cells infected with the Flag-E2 JFH1 virus were performed and the results that PHB1 and 2 co-precipitated with HCV E2 have been confirmed. Further, the PHB-E2 association does not require the presence of other viral components as demonstrated by co-immunoprecipitation (Co-IP) studies.

Figure 1A:
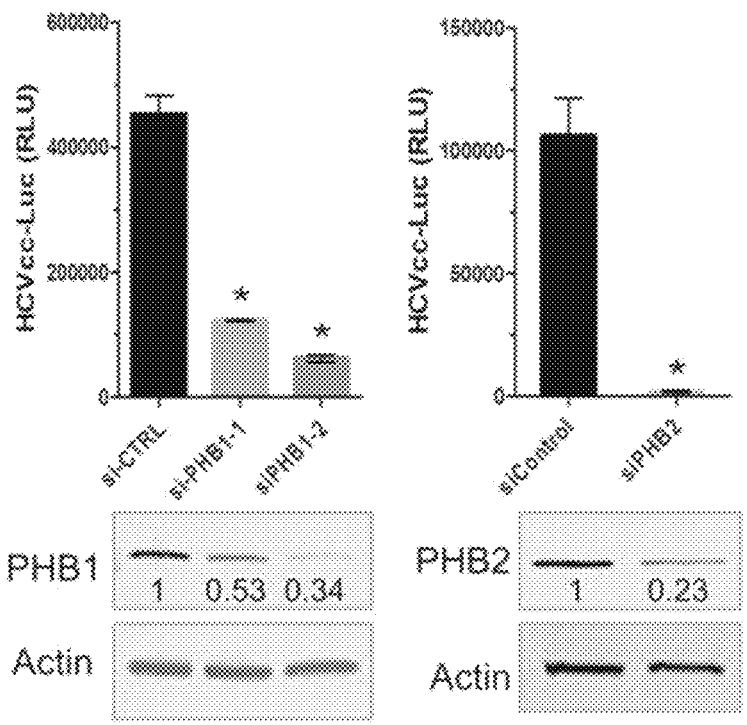
FIGS. 1A-F show that endogenous PHB1 and PHB2 are required for HCV infection. (A-B) Endogenous PHB1 and 2 were knocked down by siRNA transfection followed by HCVcc-Luc infection (MOI~0.3). Numbers shown below Western blot gel images indicate the relative expression levels quantified by Odyssey imaging system (LI-COR Biosciences). Luciferase activity was determined 72 h post-infection (A), intracellular viral RNA was quantified by RT-qPCR using protocols described in Experimental Procedures (B). Data are shown as mean±SD, $*p<0.05$. (C) Knockdown of PHB1 and 2 inHuh7.5.1 (left) or PHHs (right) were achieved by transfecting cells with relevant siRNA for 48 h. Cells were infected by HCVpp (H77) or VSV-Gpp (MOI~0.5). The percent of infection in cells transfected with si-CTRL (control) was arbitrarily set to 100% (mean±SD, $*p<0.05$). (D) Huh7.5.1 were first transfected with siRNA targeting PHB1 and 2 and then infected by HCVpp bearing glycoproteins derived from genotypes 1a, 2b, 3a, and 4c. (mean±SD, $*p<0.05$). (E & F) Restoration of HCV entry in PHBs knockdown cells by exogenously expressing PHB1 & 2. Silencing PHB1 (E) or 2 (F) by siRNA in Huh7.5.1 stable clones containing a control vector (Dox-CTRL) or a siRNA-resistant PHB-Myc (Dox-PHB1 & 2) expressing plasmid. Doxycycline was added to induce the expression of PHB-Myc. Cells were then infected by HCVcc-Luc for luciferase assay. The Western blot images were shown at the bottom of each panel to confirm the specific induction of PHB-Myc.
Figure 1B:
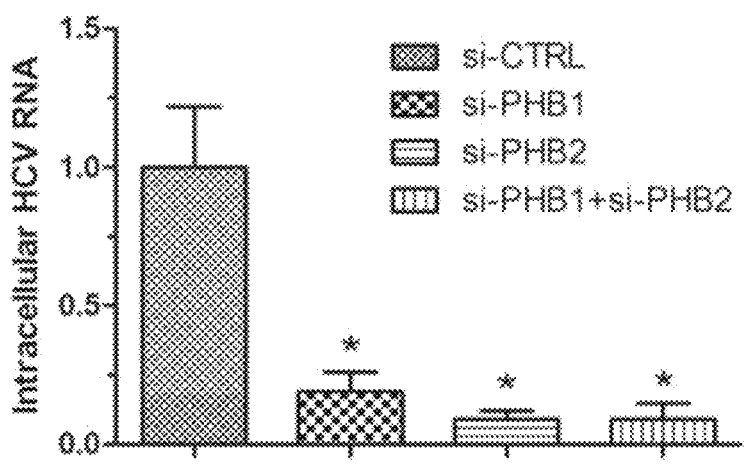

Referring to FIGS. 1A and 1B, the role of PHB in modulating HCV infection were investigated. Huh7.5.1 cells were transfected with siRNA targeting PHB1 and PHB2, respectively. Reduction of endogenous PHB1 or 2 significantly inhibited cell culture grown HCV (HCVcc) as measured by either luciferase assays (FIG. 1A) or real-time PCR quantification of viral RNA (FIG. 1B). By contrast, PHB knockdown had no effect at viral RNA levels if the infection took place first, suggesting that PHBs are required at an early stage of HCV infection. In addition, PHB1 and PHB2 knockdown also decreased the protein levels of each other.

Figure 1C:
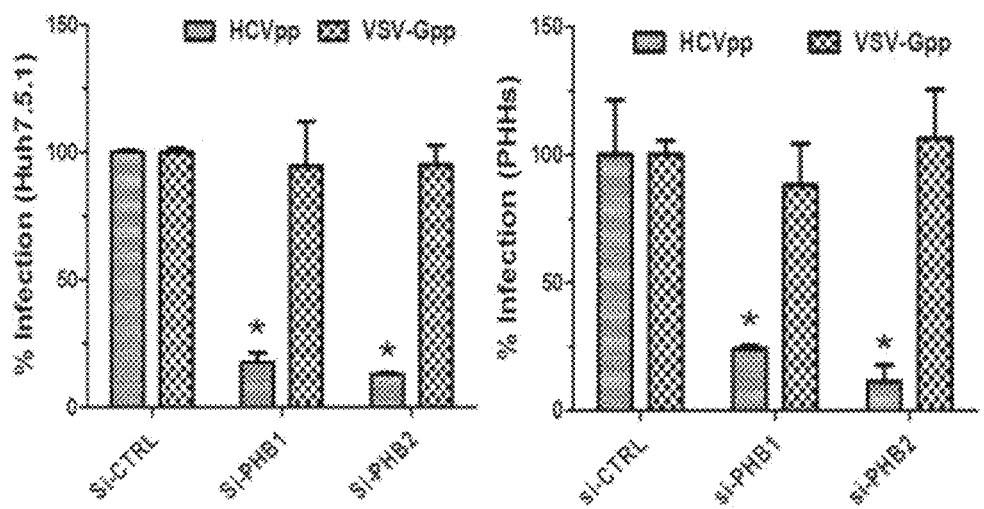
Figure 1D:
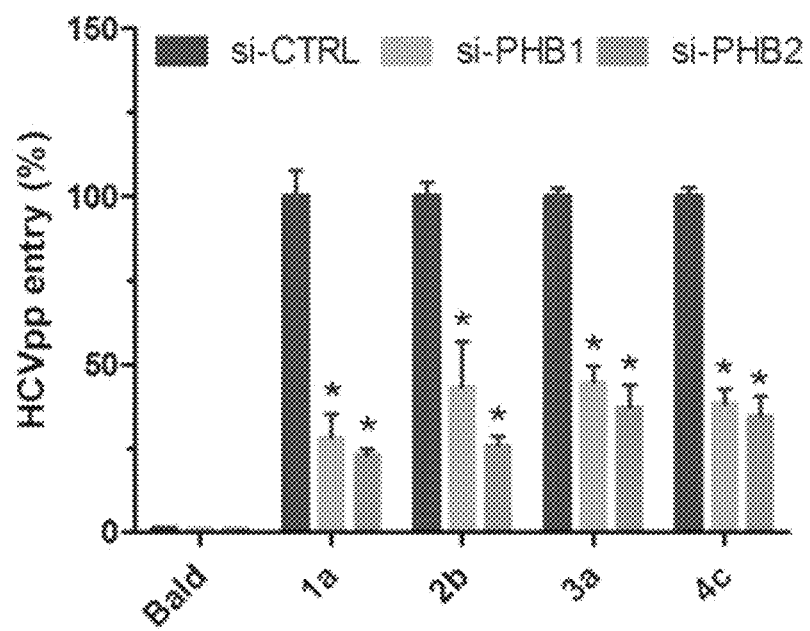

FIG. 1C shows that PHB1 and 2 are both required for HCV entry into cells. Silencing PHB1/2 in Huh7.5.1 cells or primary human hepatocytes (PHHs) ablated HIV-HCV pseudotype (HCVpp) infection while had no effect on pseudotyped virus displaying vesicular stomatitis virus G protein (VSV-Gpp) (FIG. 1C). Furthermore, FIG. 1D illustrates that PHB knockdown significantly reduced the infection of HCVpp-bearing glycoproteins from various HCV genotypes. When tested in a HCV replicon cell line, however, knockdown of endogenous PHB1 and 2 did not decrease viral RNA replication or protein translation. A HCV replicon cell line is known in the art to be used to study HCV replications.

Figure 1E:
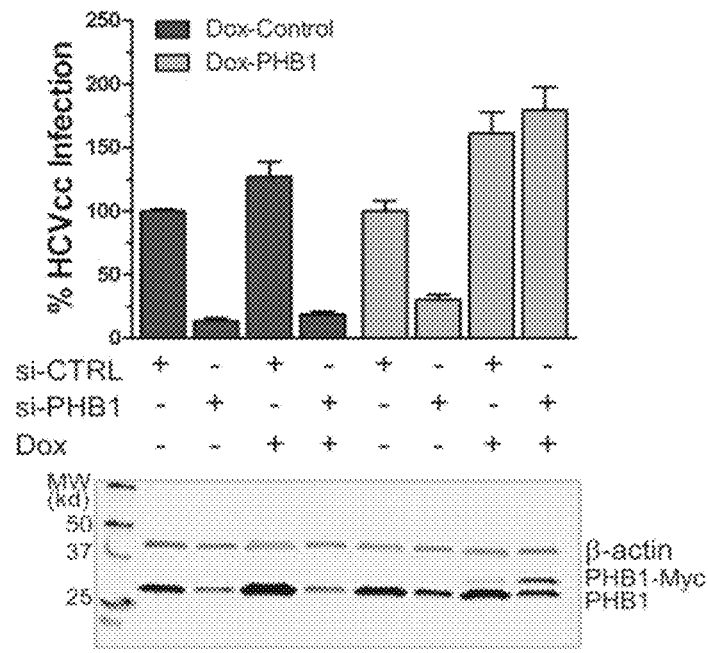
Figure 1F:
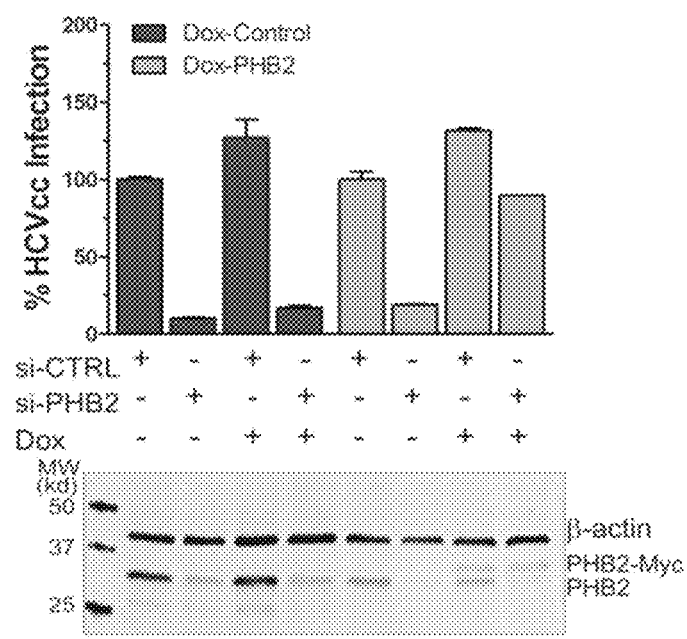

Further, Huh7.5.1 stable clones in which the PHB1 and 2 expressions are regulated by doxycycline were generated to exclude the off-target effects of siRNAs. PHB1 or 2 silencing rendered these cells less susceptible to HCV infection. However, induction of siRNA-resistant PHB1 or PHB2 restored cell susceptibility to HCVcc infection (FIG. 1E and F).

Figure 2D:
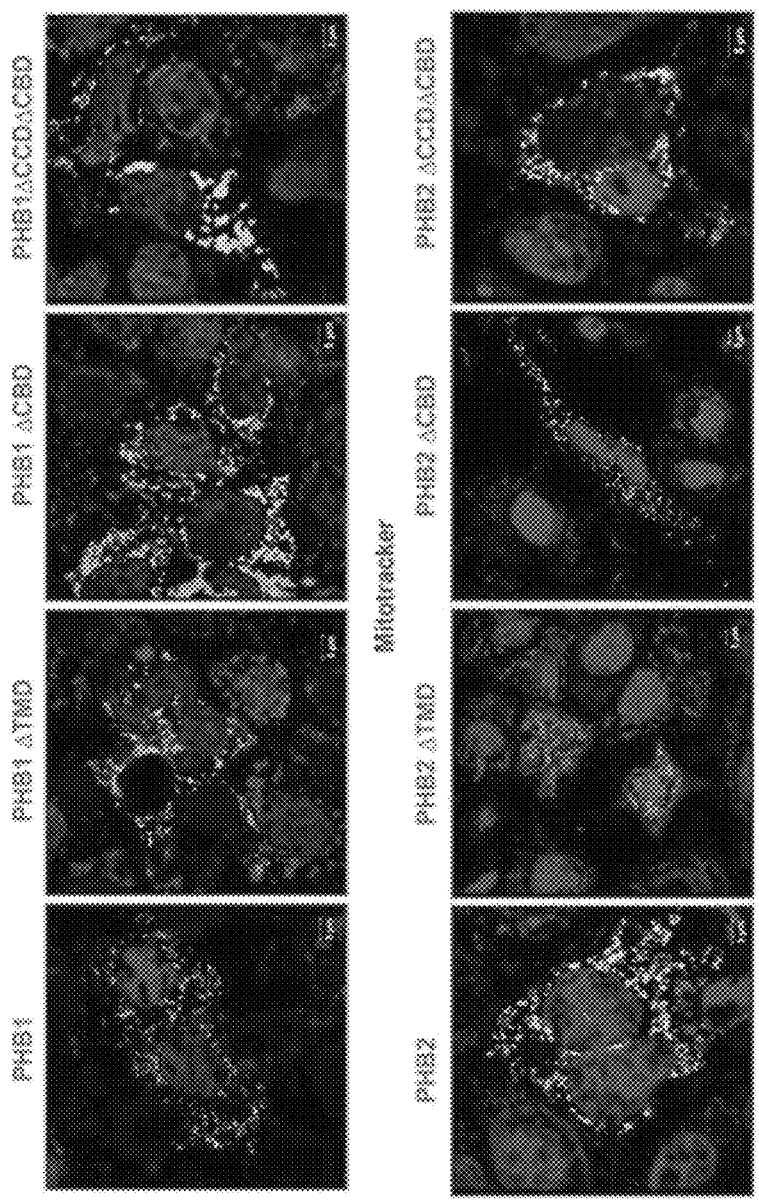

Furthermore, FIGS. 2A-2G illustrate the cellular distribution pattern of PHB1/2, which correlates with the roles of PHBs in HCV entry. Found in the inner membrane of mitochondria, PHB1 and 2 form a large multimeric complex to stabilize newly synthesized mitochondrial proteins. In addition, PHB1 and 2 are present on the plasma membrane, cytosol, and nucleus. Confocal microscopy study of endogenous PHB1 and 2 in Huh7.5 cells revealed a typical mitochondria localization pattern, although a small portion of PHB2 appeared to traffic to the cell surface. Referring to FIG. 2A, both PHB1 and 2 were detected in the pull-down product, where cell surface proteins were biotinylated then purified using streptavidin agarose beads, confirming their presence on the plasma membrane. FIG. 2A further indicates that PHB1 and 2 traffic to plasma membrane. Additionally, FIG. 2A shows that HCV infection did not change the amount of PHB1 and 2 that were found in the precipitates.

As illustrated in FIG. 2B, PHBs contain several functional domains. FIG. 2C shows that only the removal of the transmembrane domain (TMD) of PHBs led to the loss of cell surface localization during mutational studies. FIGS. 2D and 2E show that upon removal of their C-terminal domains, PHBs preserved both their cell surface and mitochondrial location, yet were unable to interact with HCV E2.

FIGS. 2G and 2F suggest that PHB1 and 2 are involved in a late stage during virus entry. To further investigate the mechanistic action of PHB, the role of PHB on binding of HCV to the cell surface were directly evaluated. HCV virions were incubated with PHB knockdown cells at 4° C. for 2 h to allow binding, which is used herein to refer to the attachment of virus particles to the surface of a cell, but not penetration, which is used herein to refer to penetration of cell plasma membrane by a viral particle. After extensive wash, surface-bound virions were quantified by measuring the abundance of viral RNA. FIG. 2F shows that PHB silencing has no effect on binding of HCV to cells and the amount of viral RNA bound to PHB knockdown cells was comparable to that of si-CTRL cells. Similarly, PHB knockdown did not have significant effect on CD81, SR-BI, CLDN1, or OCLN expression, nor did PHBs interact with any of these known entry factors. Further, the HCV E1E2-dependent fusion was measured and found that PHB knockdown cells were impaired in fusing with 293T cells expressing HCV E1E2 (FIG. 2G).

Additionally, the PHB-CRaf pathway is critical for HCV infection. Co-IP studies showed that PHB1 and 2 interact with EGFR and CRaf. Removal of the entire C-terminal domains of PHB1 and 2 abolished the interaction between PHB and CRaf. Silencing CRaf expression in Huh7.5.1 cells specifically suppressed HCV entry.

FIGS. 3A-3G show that targeting the PHB-CRaf pathway is a viable approach to block HCV infection. In certain embodiments, a therapeutically effective dosage of a compound having a structure 1 is administered to target the PHB-CRaf pathway.

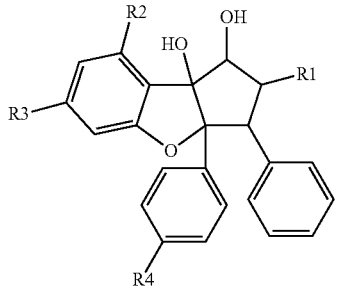

1

In certain embodiments, R1 from the structure 1 is selected from the group consisting of hydrogen, carboxyl, —C—OH,

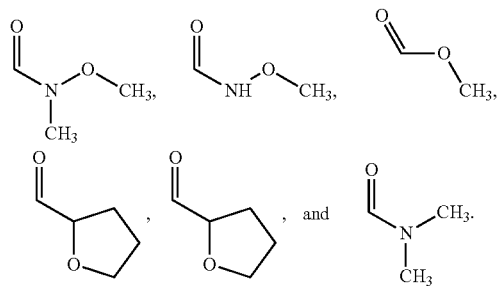

In certain embodiments, R2 from the structure 1 is selected from the group consisting of fluorine, hydrogen, and —OCH3. In certain embodiments, R3 from the structure 1 is selected from the group consisting of fluorine, hydrogen, —OCH$_3$,

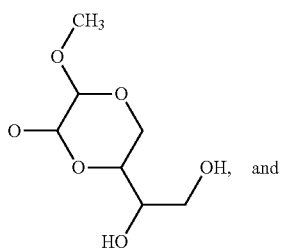

OH, and

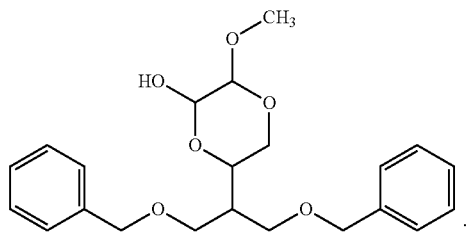

In a preferred embodiment, R1 from the structure 1 is

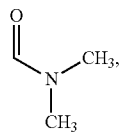

and R2 from the structure 1 is —OCH3, R3 from the structure 1 is —OCH$_3$, and R4 from the structure 1 is —OCH3, which is a natural product rocaglamide A (Roc-A).

Figure 3E:
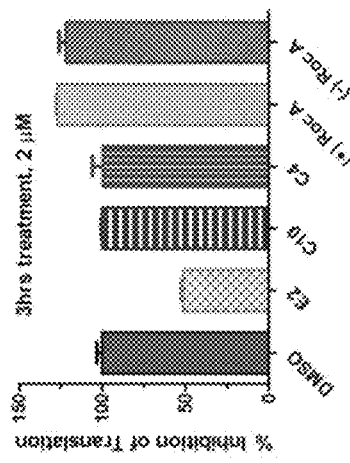

FIG. 3E shows that in certain embodiments, the chirality of Roc-A has effect on the effectiveness of inhibiting HCV infection and that the natural (−) enantiomer of Roc-A displayed stronger inhibition on HCV entry than the (+) enantiomer. Further, in some embodiments, Roc-A reduces HCVcc, HCVpp, CHIKVpp (FIGS. 4A and 4B), and dengue virus (FIG. 5) infection at low nanomolar concentrations. Additionally, Roc-A displayed a half-life of 37 minutes in a human liver microsomal stability assay, suggesting that the compound has good metabolic stability considering 45 minutes-2 hours as a targeted range for metabolic stability.

In other embodiments, a therapeutically effective dosage of a rocaglate derivative having a structure 5 is administered to target the PHB-CRaf pathway

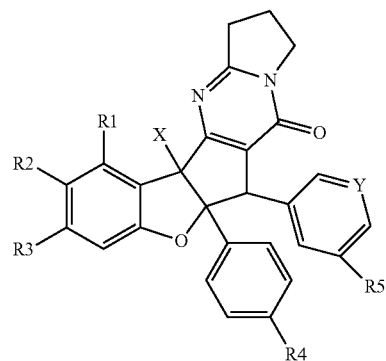

5

In certain embodiments, X is OH, Y is selected from the group consisting of C and N, R1 is selected from the group consisting of hydrogen and —OCH$_3$, R2 is selected from the group consisting of hydrogen, chloride, and —(CH$_3$)O$_2$, R3 is selected from the group consisting of fluorine and hydrogen, R4 is selected from the group consisting of chloride and hydrogen, and R5 is selected from the group consisting of hydrogen and —NHAc.

In a preferred embodiment, Y is C, R1, R3, and R4 from the structure 5 is —OCH3, and R2 and R5 is hydrogen, which is aglaroxin C. This embodiment shows that chirality of compounds has effects on inhibition of HCV cells. In some embodiments, the chiral, racemic version of the natural product aglaroxin C exhibited picomolar half-maximum effective concentrations (EC50) towards the JFH-1 genotype 2a infectious virus in cell culture and a therapeutic index (TI) of over 100 (Table 1). The term $EC_{50}$ refers to the concentration of a drug or antibody which induces a response halfway between the baseline and maximum after a specified exposure time. It is commonly used as a measure of drug's potency. The 50% cytotoxic concentration ($CC_{50}$) is defined as the quantity of a toxicant generating 50% of cell viability, compared to the control. The values of the percentages of cell viability were plotted against toxicant concentrations, and $CC_{50}$ is determined. (TI) is a comparison of the amount of a therapeutic agent that causes the therapeutic effect to the amount that causes toxicity. Further analysis indicated that in certain embodiments, (−)-aglaroxin C is the active enantiomer for HCV viral entry inhibition.

TABLE 1

Evaluation of Rocaglate Derivatives as HCV Viral Entry Inhibitors

| Compound | Structure | $EC_{50}$ | $CC_{50}$ | TI ($CC_{50}$/$EC_{50}$) | Translation inhibition at 2 μM[3] |
|---|---|---|---|---|---|
| (+) Roc-A | 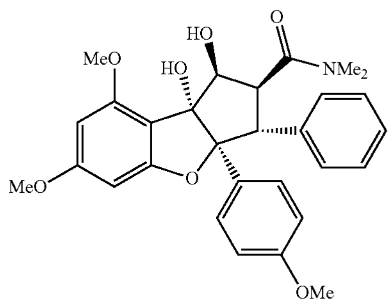 [SMILES: COc1ccc([C@]23Oc4cc(OC)cc(OC)c4[C@@]2(O)[C@@H](O)[C@@H](C(=O)N(C)C)[C@@H]3c2ccccc2)cc1] | >200 μM[1] | 300 μM[1] | N/A | No |
| (−) Roc-A | 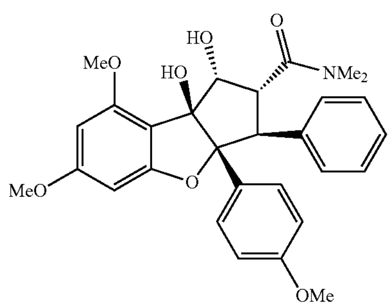 [SMILES: COc1ccc([C@@]23Oc4cc(OC)cc(OC)c4[C@]2(O)[C@H](O)[C@H](C(=O)N(C)C)[C@H]3c2ccccc2)cc1] | 1 μM[1]<br>4 nM[2] | 50 μM[1]<br>300 nM[2] | 50[1]<br>75[2] | No |
| (±) aglaroxin C (C10)* | 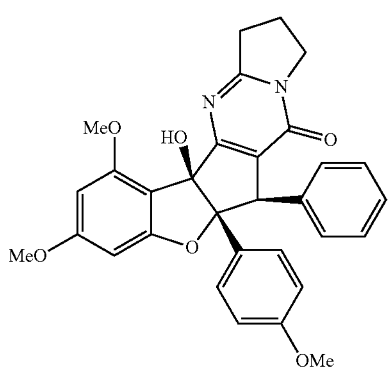 [SMILES: COc1ccc([C@@]23Oc4cc(OC)cc(OC)c4[C@]2(O)c2nc4n(c(=O)c2[C@H]3c2ccccc2)CCC4)cc1] | 100 nM[1]<br>40 pM[2] | 10 μM[1]<br>20 nM[2] | 100[1]<br>500[2] | No |
| (+)-aglaroxin C | 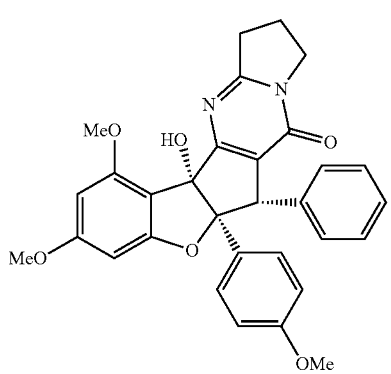 [SMILES: COc1ccc([C@]23Oc4cc(OC)cc(OC)c4[C@@]2(O)c2nc4n(c(=O)c2[C@@H]3c2ccccc2)CCC4)cc1] | 20 μM[1] | 100 μM[1] | 5[1] | No |

TABLE 1-continued

Evaluation of Rocaglate Derivatives as HCV Viral Entry Inhibitors

| Compound | Structure | $EC_{50}$ | $CC_{50}$ | TI ($CC_{50}/EC_{50}$) | Translation inhibition at 2 μM[3] |
|---|---|---|---|---|---|
| (−)-aglaroxin C | 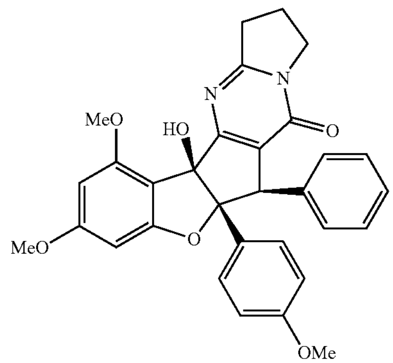 [SMILES: COc1ccc([C@@]23Oc4cc(OC)cc(OC)c4[C@]2(O)c2nc4n(c(=O)c2[C@H]3c2ccccc2)CCC4)cc1] | 200 nM[1] | 12 μM[1] | 60[1] | No |

[1]Compounds were incubated with cells for a total of 3 h on Huh7.5.1 cells.
[2]Compounds were incubated with cells for a total of 48 h on Huh7.5.1 cells.
[3]Measured using a luciferase reporter gene that was transfected into Huh7.5.1 cells. The compound was added for 3 h.
*Name appearing in FIG. 3G.

Figure 3F:
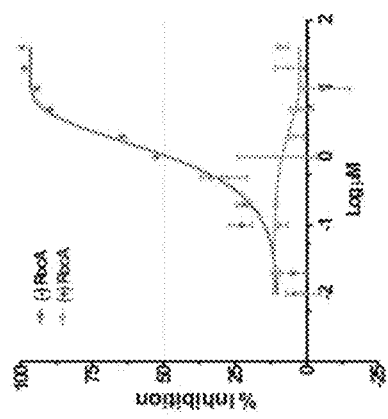
Figure 3G:
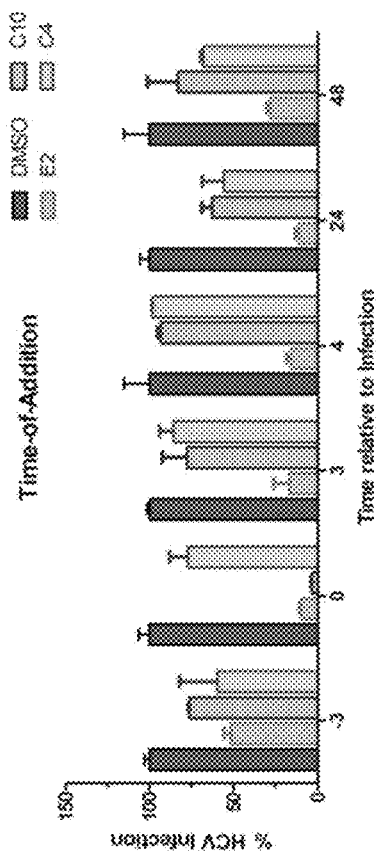

Referring to FIG. 3G, in certain embodiments, chiral, racemic aglaroxin C displayed maximal anti-HCV activity when added together with the virus but lost its activity when added about 3 h after the infection was initiated.

In yet other embodiments, a therapeutically effective dosage of a compound having the following structure:

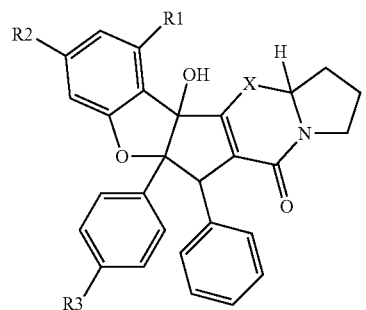

wherein X is selected from a group consisting of oxygen and nitrogen, R1 is —OCH$_3$, R2 is —OCH$_3$, and R3 is —OCH$_3$.

In yet other embodiments, a therapeutically effective dosage of a compound having a following structure:

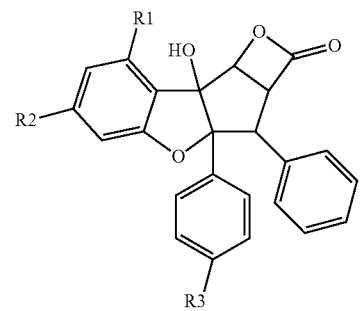

is administered to a subject, wherein R1 is selected from the group consisting of hydrogen and —OCH$_3$, R2 is selected from the group consisting of hydrogen and —OCH$_3$, and R3 is selected from the group consisting of bromine, hydrogen, and —OCH$_3$.

Several derivative compounds of aglaroxin C have also been synthesized and tested. In certain embodiments, a compound is administered to target HCV entry having a following structure 9:

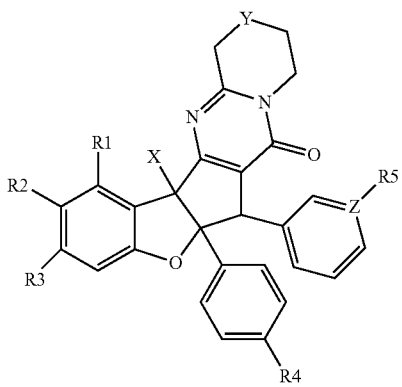

wherein X is OH, Y is selected from the group consisting of C and O, Z is selected from the group consisting of C and N, R1 is selected from the group consisting of hydrogen and —OCH$_3$, R2 is selected from the group consisting of hydrogen and chloride, R3 is selected from the group consisting of hydrogen and —OCH$_3$, R4 is selected from the group consisting of hydrogen, chloride, and —OCH$_3$, and R5 is selected from the group consisting of hydrogen and fluorine.

In a preferred embodiment, Y is C, Z is N, R1 is hydrogen, R2 is chloride, and R3 is hydrogen, R4 is chloride, and R5 is hydrogen and the compound comprises a tPSA of about 74.49 and a CLogP of about 3.7135. Further, the compound comprises a structure 11:

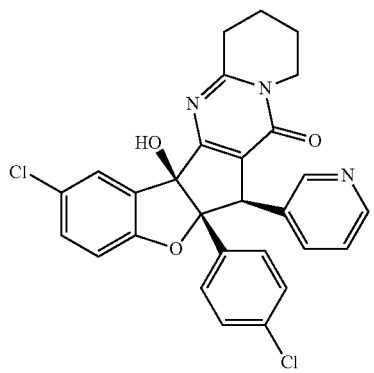

11

In another preferred embodiment, Y is O, Z is N, R1 is hydrogen, R2 is chloride, R3 s hydrogen, R4 is hydrogen, and R5 is hydrogen and the compound comprises a tPSA of about 83.72 and a CLogP of about 1.3725. Further, the compound comprises a structure 12:

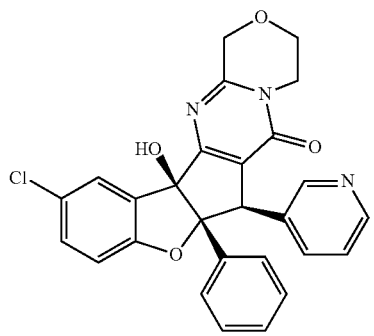

12

In yet other preferred embodiment, Y is C, Z is C, R1 is hydrogen, R2 is hydrogen, and R3 is —OCH₃, R4 is hydrogen, and R5 is hydrogen and the compound comprises a tPSA of about 71.36 and a CLogP of about 3.7335. Further, the compound comprises a structure 13:

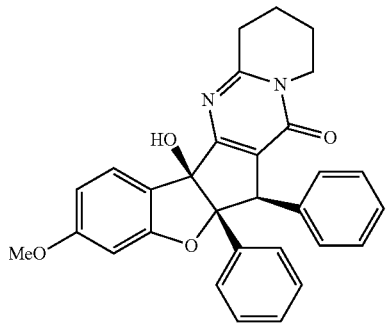

13

In other embodiments, a compound is administered to target HCV entry having a following structure 14:

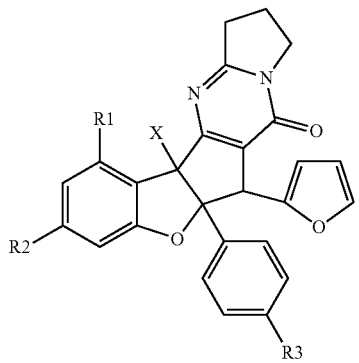

14 wherein X is OH, R1 is selected from the group consisting of fluorine and —OCH₃, R2 is fluorine, and R3 is chloride.

In a preferred embodiment, R1 is —OCH₃, R2 is fluorine, and R3 is chloride and the compound comprises a tPSA of about 80.59 and a CLogP of about 3.278. Further, the compound comprises a structure 15:

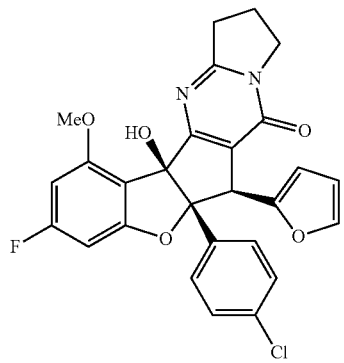

15

In other preferred embodiment, R1 is fluorine, R2 is fluorine, and R3 is chloride and the compound comprises a tPSA of about 71.36 and a CLogP of about 3.4495. Further, the compound comprises a structure 16:

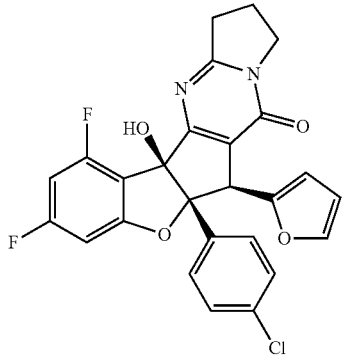

16

EXAMPLE 1

A PHB Inhibitor, Rocaglamide A (Roc-A), Inhibits HCV Entry

Materials and Methods
Immunofluorescence Staining and Confocal Microscopy

Detailed procedures have been published (Yang et al., 2008). In brief, cells were stained with mitotracker red (1:10,000) at 37° C. for 15 min and then fixed in −20° C. cold methanol for 5 min. Antibody dilutions are: anti-PHB1 (Santa Cruz, E-5 clone, 1:200), anti-PHB2 (Millipore, Cat No. 07-234, 1:200). Secondary antibodies were Alexa Fluor 488 or 568 Goat Anti-Mouse or Rabbit IgG (Life technologies 1:1000). Images were captured by a Zeiss LSM 700 laser scanning microscope.

HCV E1E2-Mediated Cell-Cell Fusion Assay

Detailed protocols have been published (Si et al., 2012). In brief, Huh7.5.1 cells were transfected with si-CTRL (control siRNA), or si-PHB1, or si-PHB2, and Stop-Luc construct which contains a firefly luciferase reporter gene whose transcription is prevented by a Stop cassette flanked by LoxP sites. 48 h post-transfection, these recipient cells were mixed at a 1:1 ratio with 293T-CLDN1 cells expressing Cre and HCV E1E2 (H77, genotype 1a) (donor cells) to initiate cell-cell fusion. Luciferase activity was measured 24 h thereafter.

Cell Surface Biotinylation Assay

Huh7.5.1 cells from four 150 mm plates were treated with DMSO, Roc-A (20 nM), or infected by HCVcc. 48 h post-transfection, cells were washed three times with ice-cold PBS and resuspended in PBS at a density of 25×106 cells/ml. Freshly prepared Sulfo-NHS-SS-biotin (Pierce) was added to the cells (final concentration 0.5 μg/ml) and allowed to incubate at 4° C. for 30 min. Cells were then washed three times with ice-cold PBS. 25 mM Tris (pH 8.0) was added in the initial wash to quench any non-reacted biotin reagent. Following cell lysis in RIPA buffer (50 mM Tris-HCl [pH 7.5], 150 mM NaCl, 1% NP-40, 0.25% sodium deoxycholate, 1 mM EDTA, 2 mM Na3VO4 and Pierce protease inhibitor cocktail), lysates were cleared by centrifugation at 13,000×g for 15 min at 4° C. The cleared lysates were used for immunoprecipitation using a 1:1 mixture of Streptavidin beads (Pierce). Beads were washed three times with RIPA buffer, and bound proteins were eluted by boiling the samples in SDS-PAGE sample buffer and then resolved on 9% SDS-PAGE. Biotinylated proteins were detected by anti-PHB1 and anti-PHB2 antibodies.

Cytotoxicity/Cell Viability Assay

PHHs (105 per well) were treated with Roc-A or DMSO at various concentrations for 48 h in 48-well plates. The numbers of viable cells in culture were determined using the CellTiter-Glo Cell Viability Luminescent Assay kit according to the manufacturer's instruction (Promega).

Statistical Analysis

Bar graphs were plotted to show mean ±standard deviation (SD) of at least two independent experiments. Statistical analyses were performed using Graphpad Prism 5. A p value of b0.05 in the Student's test was considered statistically significant.

Chemical Synthesis

Synthetic rocaglates and derivatives were obtained from the chemical collection at the BU Center for Molecular Discovery (BU-CMD). Chiral, racemic rocaglates (Roche et al., 2010a, 2010b) and rocaglate hydroxamates (Rodrigo et al., 2012) were synthesized using the reported procedures. Chiral, non-racemic (−)-aglaroxin C and (+)-aglaroxin C were synthesized using biomimetic kinetic resolution of chiral, racemic aglain ketone precursors according to the published protocol (Stone et al., 2015) followed by further chemical transformations. (−)-Roc-A, and (+)-Roc-A were synthesized using the same protocol followed by amide formation (Gerard et al., 2006).

FIGS. 3A-3G show that targeting the PHB-CRaf pathway is a viable approach to block HCV infection. The natural product rocaglamide A (Roc-A) has been shown to directly bind to PHB1 and 2 and blocks PHB-CRaf-MEK-ERK signaling (Polier et al., 2012). Addition of Roc-A at 20 nM did not inhibit HCV RNA replication or protein translation (FIGS. 3A and 3B). Rather, it significantly reduced HCVcc, HCVpp, CHIKVpp, and dengue virus infection at low nanomolar concentrations. Moreover, pretreatment of PHHs with Roc-A at non-cytotoxic concentrations also suppressed HCVpp entry (FIG. 3A). The therapeutic index (TI) of Roc-A is greater than 80 when tested on primary human hepatocytes. Notably, Roc-A treatment decreased the cell surface expression of PHB1 and 2 (FIG. 2A) and also decreased PHB1, 2, Ras, and CRaf at the total protein level (FIG. 3B). Roc-A treatment disrupted the PHB-CRaf interaction in a co-IP experiment (FIG. 3C and D). Finally, Roc-A displayed a half-life of 37 min in a human liver microsomal stability assay, suggesting that the compound has good metabolic stability.

EXAMPLE 2

Roc-A Derivatives Display Improved Therapeutic Index

To obtain compounds that display more favorable therapeutic index towards HCV, we evaluated a set of 32 additional rocaglate derivatives to ascertain structure-activity relationships (SAR). Interestingly, the natural (−) enantiomer of Roc-A displayed stronger inhibition on HCV entry than the (+) enantiomer (FIG. 3E). Moreover, the chiral, racemic version of the natural product aglaroxin C (Udom Kokpol, 1994) exhibited picomolar half-maximum effective concentrations (EC50) towards the JFH-1 genotype 2a infectious virus in cell culture and a therapeutic index of over 100 (Table 1). Further analysis indicated that (−)-aglaroxin C is the active enantiomer for HCV viral entry inhibition (Table 1). Moreover, these compounds, even when incubated at 2 μM for 3 h, did not inhibit protein translation (FIG. 3F). Results from a time-of-addition experiment further showed that chiral, racemic aglaroxin C displayed maximal anti-HCV activity when added together with the virus but lost its activity when added 3 h after the infection was initiated (FIG. 3G). This finding bolstered the notion that aglaroxin C is specifically inhibiting HCV viral entry.

DISCUSSION

The identification of PHB1 and 2 as HCV entry factors is somewhat surprising because these two proteins are typically recognized as molecular chaperones that stabilize other mitochondrial proteins. A fraction of PHB1 and 2 can be found on the surface of Huh7.5.1 cells, although they are not required for the initial binding of virions. Given that PHB-CRaf interaction is necessary for CRaf activation by Ras (Rajalingam and Rudel, 2005; Polier et al., 2012), and that HRas is a key host signal transducer for EGFR-mediated HCV entry (Zona et al., 2013), a plausible role of PHBs in HCV entry is to link HRas to CRaf-mediated signaling. In support of this notion, we found that CRaf knockdown reduced HCV infection, as did disruption of PHB-CRaf interaction by Roc-A. PHBs have been implicated in facilitating signal transduction. For example, a recent study showed that PHB1, normally stored in mast cell granules, translocates to plasma membrane lipid rafts upon antigen stimulation in order to activate the tyrosine kinase Syk-dependent signaling that stimulates mast cell degranulation and the secretion of cytokines (28).

Exactly when and how HCV activates the PHBs-mediated signaling remains to be investigated. PHB1/2 do not precipitate with CD81, SR-BI, CLDN1, or OCLN, but are associated with HCV E2 in both infected and co-transfected cells. PHBs are anchored to the plasma membrane or mitochondrial inner membrane by their transmembrane domains with carboxyl termini facing cytoplasm or the intermembrane space of mitochondria. The C-termini of PHBs recruit CRaf to the inner plasma membrane (Mishra et al., 2005). Given that HCV E2 does not traffic to the intermembrane space of mitochondria, the interaction between PHBs and E2 likely takes place in close proximity to the inner plasma membrane although evidence for direct PHB-HCV E2 interaction is still lacking. Since the removal of either the transmembrane domain or C-terminal domain of PHBs abolishes PHB-E2 interaction, HCV E2 may form a signaling complex with membrane-bound PHB-CRaf at some point during entry. The PHBs-HCV E2 associations are not mediated by cell membranes, as C-terminal deletion of PHBs did not alter their membrane localization. C-terminal deletion did, however, abolish PHBs-E2 association. Plasma membrane-bound PHB1 is indispensable for the activation of CRaf by Ras (Rajalingam and Rudel, 2005; Rajalingam et al., 2005), and interaction between PHB1 and CRaf requires phosphorylation of PHB1 at Thr 258 and Tyr 259 (Chiu et al., 2013). Further investigation is needed to understand the topology, the phosphorylation status of plasma membrane-bound PHBs, and the likely signaling pathways that PHBs mediate during HCV entry.

An exciting finding of our study is that Roc-A, which binds PHB and inhibits its interaction with CRaf (Polier et al., 2012), potently inhibited HCV entry. Roc-A was first reported as an immunosuppressant and inhibitor of NF-kappa B activity (31). Roc-A and related rocaglates are also recognized as potent anticancer compounds (Kim et al., 2006; Ebada et al., 2011) by inhibiting translation initiation through inhibition of the RNA helicase eIF4a (Roche et al., 2010a, 2010b; Rodrigo et al., 2012; Chowdhury et al., 2014; Cencic et al., 2009). Roc-A has also been shown to indirectly target heat shock factor 1 (HSF1), amultifaceted transcriptional regulator of the heat-shock response and numerous other cellular processes essential for anabolic metabolism, cellular proliferation, and tumorigenesis (Santagata et al., 2013). In the current study, Roc-A treatment significantly reduced the protein levels of cell surface-bound PHB1 and PHB2 and disrupted PHB-CRaf interaction, indicating that it blocks HCV entry by targeting this pathway. The observation that a racemic, synthetic sample of the natural product aglaroxin C displays improved therapeutic index relative to enantiopure Roc-A suggests the possibility for synergy of both (+) and (−) enantiomers (Zhuang et al., 2014; Danielsson et al., 2011). In our studies, chiral, racemic aglaroxin C did not inhibit protein translation even at 2 μM over 3 h in a translation inhibition assay (FIG. 3F). Future investigations will be needed to understand whether it is possible to selectively target the PHB-CRaf pathway using appropriately functionalized rocaglates (flavaglines) and to what extent there may be synergy between translation inhibition or other mechanisms and HCV viral entry effects via PHB's (Cencic et al., 2010; Rozelle et al., 2014).

In conclusion, the identification of PHB1 and 2 adds additional targets to the repertoire of HCV entry factors. In contrast to most small molecule inhibitors that have advanced to the clinic targeting viral components, Roc-A, a PHB inhibitor, represents a promising drug lead that targets a host factor and hence reduces the likelihood that resistance will be developed. By virtue of its distinct mechanism of inhibition, Roc-A and its derivatives may also be used in combination with other anti-HCV drugs for potential synergistic effects in treating HCV infections, especially in settings where liver cancer is present. The observation that rocaglates (flavaglines) block CHIKVpp entry and dengue virus infection also raises the hope that Roc-A or an optimized congener may be developed into a drug curbing infections by the two viruses.

While the invention is described through the above-described exemplary embodiments, it will be understood by those of ordinary skill in the art that modifications to, and variations of, the illustrated embodiments may be made without departing from the inventive concepts disclosed herein. Disclosed aspects, or portions of these aspects, may be combined in ways not listed above. Accordingly, the invention should not be viewed as being limited to the disclosed embodiment(s).

We claim:

1. A method to inhibit hepatitis C viral infection by administering to a subject a therapeutically effective dosage of a compound having a structure of compound 2:

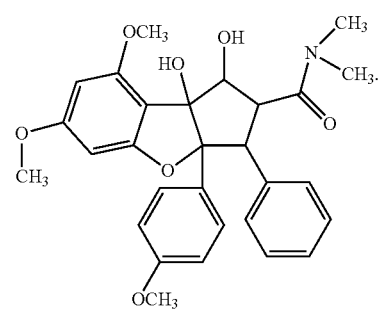

2. The method of claim 1, wherein compound 2 comprises compound 3:

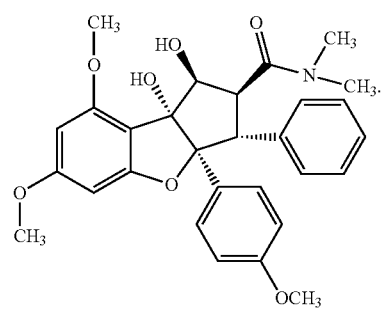

3. The method of claim 2, wherein compound 3 comprises an EC50≥about 200 μM, and a CC50 of about 300 μM when incubated with cells for about 3 hours.

4. The method of claim 1, wherein:
compound 2 comprises compound 4:

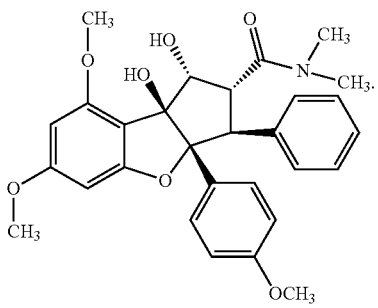

4

5. The method of claim 4, wherein compound 4 comprises an EC50 of about 1 µM, a CC50 of about 50 µM, and a TI (CC50/EC50) of about 50, when incubated with cells for about 3 hours.

6. The method of claim 4, wherein compound 4 comprises an EC50 of about 4 nM, a CC50 of about 300 nM, and a TI of about 75, when incubated with cells for about 48 hours.

7. A method to inhibit hepatitis C viral infection by administering to a subject a therapeutically effective dosage of a compound having a structure of compound 6:

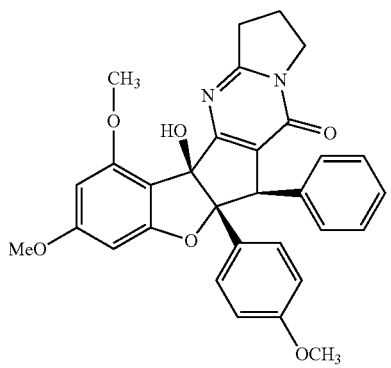

6 wherein compound 6 is chiral, racemic and comprises both (+) or (−) enantiomers.

8. The method of claim 7, wherein compound 6 comprises an EC50 of about 100 nM, a CC50 of about 10 µM, and a TI (CC50/EC50) of about 100, when incubated with cells for about 3 hours.

9. The method of claim 7, wherein compound 6 comprises an EC50 of about 40 pM, a CC50 of about 20 nM, and a TI (CC50/EC50) of about 500, when incubated with cells for about 48 hours.

10. The method of claim 7, wherein compound 6 comprises compound 7:

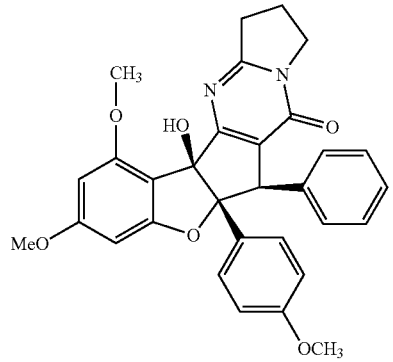

7 wherein compound 7 at C10 is NOT racemic.

11. The method of claim 10, wherein compound 7 comprises an EC50 of about 200 nM, a CC50 of about 12 µM, and a TI (CC50/EC50) of about 60, when incubated with cells for about 3 hours.

12. The method of claim 7, wherein compound 6 comprises compound 8:

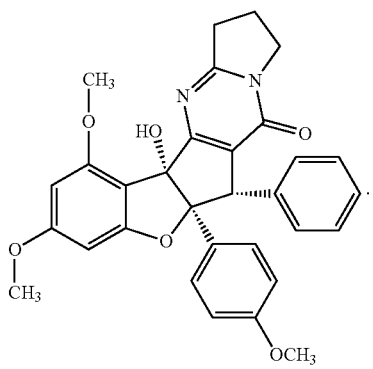

8

13. The method of claim 12, wherein compound 8 comprises an EC50 of about 20 µM, a CC50 of about 100 µM, and a TI (CC50/EC50) of about 5, when incubated with cells for about 3 hours.

* * * * *